United States Patent
Allbritton et al.

(10) Patent No.: US 7,759,119 B2
(45) Date of Patent: Jul. 20, 2010

(54) SYSTEMS AND METHODS FOR EFFICIENT COLLECTION OF SINGLE CELLS AND COLONIES OF CELLS AND FAST GENERATION OF STABLE TRANSFECTANTS

(75) Inventors: Nancy Allbritton, Irvine, CA (US); Christopher E. Sims, Irvine, CA (US); Yuli Wang, Irvine, CA (US); Mark Bachman, Irvine, CA (US); Guann-Pyng Li, Irvine, CA (US); Eric Stanbridge, Corona Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 6 days.

(21) Appl. No.: 11/733,053

(22) Filed: Apr. 9, 2007

(65) Prior Publication Data

US 2007/0238122 A1    Oct. 11, 2007

Related U.S. Application Data

(60) Provisional application No. 60/744,577, filed on Apr. 10, 2006, provisional application No. 60/744,579, filed on Apr. 10, 2006.

(51) Int. Cl.
| | |
|---|---|
| *C12N 15/00* | (2006.01) |
| *C12N 5/02* | (2006.01) |
| *C12N 5/00* | (2006.01) |
| *C12N 15/01* | (2006.01) |
| *C12N 1/02* | (2006.01) |

(52) U.S. Cl. .................. 435/325; 435/440; 435/252.3; 435/173.9; 435/174

(58) Field of Classification Search ........................ None
See application file for complete search history.

(56) References Cited

U.S. PATENT DOCUMENTS

| | | | |
|---|---|---|---|
| 5,998,129 A | | 12/1999 | Schutze et al. |
| 6,090,919 A | * | 7/2000 | Cormack et al. ............. 530/350 |
| 2001/0006815 A1 | * | 7/2001 | Rabbani et al. ............. 435/440 |
| 2003/0059764 A1 | | 3/2003 | Ravkin et al. |
| 2003/0129741 A1 | | 7/2003 | Ramstad |
| 2004/0087052 A1 | | 5/2004 | Katakis et al. |

FOREIGN PATENT DOCUMENTS

| | | |
|---|---|---|
| WO | WO 97/29355 A | 8/1997 |
| WO | WO 02/094454 A1 | 11/2002 |
| WO | WO 03/16868 A | 2/2003 |
| WO | WO 03/035824 A | 5/2003 |
| WO | WO 03/039750 A | 5/2003 |
| WO | WO 2004/024328 A | 3/2004 |
| WO | WO 2006041938 A2 | 4/2006 |
| WO | WO 2006060922 A1 | 6/2006 |

OTHER PUBLICATIONS

Watson, Molecular Biology of the Gene, Third Edition, 1976, W.A. Benjamin, Inc., Menlo Park, CA, p. 62.*
Zoeller et al, Methods Enzymol. 209: 34 (1992).*
Barron, et al., "Laser Printing of Single Cells: Statistical Analysis, Cell Viability, and Stress," Annals of Biomedical Engineering, 33:2, pp. 121-130 (Feb 2005).
Langer, et al., "Live cell catapulting and recultivation does not change the karyotype of HCT116 tumor cells," Cancer Genetics an Cytogenetics, No. 161 pp. 174-177 (2005).
Stich, et al., "Live Cell Catapulting and Recultivation," Pathology Research and Practice, 199:6, pp. 405-409 (Jan 1, 2003).

* cited by examiner

*Primary Examiner*—James Martinell
(74) *Attorney, Agent, or Firm*—Orrick, Herrington & Sutcliffe LLP

(57) ABSTRACT

A plate manufactured to enable samples of cells, micro-organisms, proteins, DNA, biomolecules and other biological media to be positioned at specific locations or sites on the plate for the purpose of performing addressable analyses on the samples. Preferably, some or all of the sites are built from a removable material or as pallets so that a subset of the samples of interest can be readily isolated from the plate for further processing or analysis. The plate can contain structures or chemical treatments that enhance or promote the attachment and/or function of the samples, and that promote or assist in their analyses. Use of the plate advantageously enables the selection and sorting of cells based on dynamic phenomena and the rapid establishment of stable tranfectants.

31 Claims, 16 Drawing Sheets

STEP 1

STEP 2

STEP 3

STEP 4

STEP 5

STEP 6

STEP 7

STEP 8

STEP 5

STEP 6

STEP 7

STEP 8

(A)

(B)

(C)

(D)

(E)

(F)

(G)

(H)

(I)

(J)

(K)

Growth of Cells Off Of Released & Isolated Pallets

Cloning of Selected Cells

Cloning of Selected Cells

| 0 hr after release | 60 hr after release | 74 hr after release | 146 hr after release |

After 6 days on pallet array, release the pallets with only green cells

SYSTEMS AND METHODS FOR EFFICIENT COLLECTION OF SINGLE CELLS AND COLONIES OF CELLS AND FAST GENERATION OF STABLE TRANSFECTANTS

CROSS-REFERENCE TO RELATED APPLICATIONS DATA

This application claims the benefit of U.S. provisional patent application Nos. 60/744577, filed Apr. 10, 2006, and 60/744,579, filed Apr. 10, 2006, which applications are incorporated herein by reference.

This invention was made with Government support under Grant Nos. EB004436, EB004597 and CA104214, awarded by the National Institutes of Health. The Government has certain rights to this invention.

FIELD OF THE INVENTION

The present invention relates to biochemical analysis and, more particularly, to a micropatterned plate with micro-pallets that facilitates addressable biochemical analysis and methods that facilitate sorting and selection of cells and colonies of cells.

BACKGROUND

Modern techniques for the molecular analysis of cell biology have created an increasing need to prepare samples composed of a homogeneous population of cells. Genomic and proteomic studies, genetic cloning, stem cell studies, and cell-based screening would all benefit from an enhanced ability to obtain living, single cells or small homogeneous biological samples for subsequent analysis. These samples include various molecules such as DNA or RNA as well as cells or organisms.

In the case of selecting cells from a mixed population, individual cells possessing a desired characteristic must be analyzed followed by identification and isolation of a desired subpopulation. Standard sorting methods for mammalian cells require cells to be dispersed in a single-cell suspension, and are most successful with hematopoietic cells which grow naturally in this manner. These methods are less applicable to adherent cells, by far the most common cell phenotype.

Adherent cells are typically analyzed by plating them on a growth surface then looking for them using a microscope. The locations of the cells are random so that finding the cells can be a time consuming process. To speed this up, robotic systems that utilize machine vision are sometimes used to find the cells within the field of view of the microscope image. Traditional sorting techniques for separating cells of interest from a mixed population of cells typically require enzymatic or mechanical release of adherent cells from their growth surface which is detrimental to cell health, or involve extended protocols for selection based on limiting dilution or genetically engineered resistance to a selective environment. In some cases a sacrificial base layer is placed over the plate, cells are grown on the sacrificial base layer and, once cell of interests are found, a subset of the mixed population of cells are isolated by cutting a circle around the cells of interest and through the sacrificial layer with a high powered laser. Cells can be isolated by peeling away the sacrificial layer, or by catapulting the cut material from plate using a high powered laser pulse, carrying the cells of interest with catapulted cut material.

Nonadherent cells can be analyzed quickly using a flow cytometer that rapidly flows a stream of cells past a detector apparatus. Cells of interest can be sorted by a downstream electrostatic system that moves droplets into collection containers. Flow cytometry tends to also work for other biological media such as proteins and DNA if they can be attached to small beads. It tends not to work well for larger samples (such as multi-celled organisms) and is difficult to multiplex.

SUMMARY

The system and methods described herein provide a plate manufactured in such a way that samples such as single or multiple cells, micro-organisms, proteins, DNA, biomolecules and other biological media can be positioned at specific locations or sites on the plate for the purpose of performing addressable analyses on the samples. Furthermore, some or all of the sites are preferably built from a removable material in the form of micro-pallets so that a subset of the samples of interest can be readily isolated from the plate for further processing or analysis. The plate can contain structures or chemical treatments that enhance or promote the attachment and/or function of the samples, and that promote or assist in the analyses of the samples. The plate can also contain structures that aid in the coupling between the plate and external instruments or that aid in accessory operations, such as maintaining proper chemical conditions for the samples.

The micro-patterned plate advantageously includes (1) structures patterned on it that are intended to facilitate the attachment of samples at known locations or sites, (2) structures or pallets that are treated or further patterned to improve the ability to perform analysis on the samples, (3) structures or pallets that are removable on demand so that laser cutting is not required, and released samples can be readily collected, and (4) micro-patterned features such as structural elements, electrodes, and optical encoders that assist in the operation of the micro-array plate, and advantageously can be placed in conventional or specialized cassettes or trays. As such, the micro-patterned plate enables high speed, addressable analysis of biological and chemical samples, as well as an efficient method for isolating subsets of samples from a larger population of samples.

Use of the micro-pallet array system advantageously enables the selection and sorting of cells based on dynamic phenomena and the rapid establishment of stable tranfectants.

Further, objects and advantages of the invention will become apparent from the following detailed description.

BRIEF DESCRIPTION OF THE DRAWINGS

FIGS. 12A and C show clonal colonies of cells grown from single cells plated simultaneously on a pallet array. The individual pallets are released and collected separately to yield two clonal populations differing in their growth characteristics. FIGS. 12B and D show the cells proliferating at different rates. FIGS. 12E and F show cells plated simultaneously on a pallet array possessing different morphologies. The pallet containing the cell of the desired morphogy can be released, collected and separated from the cells with alternate morphologies.

FIGS. 13A through 13F are images that show the collection of a clonal colony stably transfected with a green fluorescent marker protein. Single cells are plated on the array such that one or fewer cells is plated on individual pallets. FIGS. 13A, C, and E are transmitted light images, whereas FIG. 13B, D, and F are the corresponding fluorescence images. FIGS. 13A and B show a single colony of a clonal population of cells expressing the fluorescent protein amongst several colonies of cells lacking that protein. FIGS. 13C and D show the pallet and fluorescent colony having been separated from the array and placed in a culture well. FIGS. 13E and F show the clonal population having proliferated into a large colony containing only fluorescent cells.

FIGS. 13 and 14 taken together demonstrate the ability to perform transmission light microscopy and fluorescence microscopy of cells growing on the pallet array over a wide range of fluorescence wavelengths.

In FIGS. 15A and C the cell is seen to remain adherent to the pallet after isolation, and then is shown to begin migration off of the pallet. In FIGS. 15B and D another cell is shown to begin proliferation after placement in the culture well.

DETAILED DESCRIPTION OF THE PREFERRED EMBODIMENT

Figure 1A:
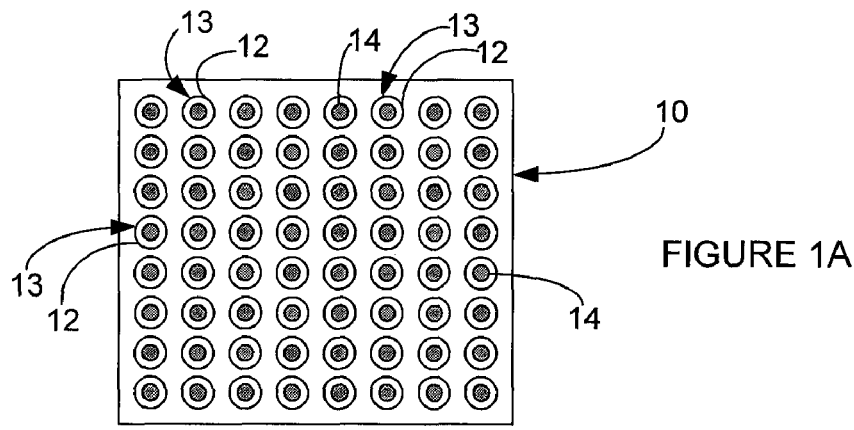
FIG. 1A is a micro-patterned plate having an array of micro-pallets.

Each of the additional features and teachings disclosed below can be utilized separately or in conjunction with other features and teachings to provide an improved micropatterned plate with micro-pallets that facilitates addressable biochemical analysis and improved methods for cell sorting and selection. Representative examples of the present invention, which examples utilize many of these additional features and teachings both separately and in combination, will now be described in further detail with reference to the attached drawings. This detailed description is merely intended to teach a person of skill in the art further details for practicing preferred aspects of the present teachings and is not intended to limit the scope of the invention. Therefore, combinations of features and steps disclosed in the following detail description can not be necessary to practice the invention in the broadest sense, and are instead taught merely to particularly describe representative examples of the present teachings.

Moreover, the various features of the representative examples and the dependent claims can be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

In a preferred embodiment, a system provides a micro-patterned plate comprising an addressable array of removable regions or sites to which samples can be attached. Optical encoders, electrodes, and the like enable the micro-patterned plate to be readily coupled to external instrumentation, enabling high speed addressable cell assays. Machines can move the plate to position any addressable site under the microscope. High magnification objectives can be used for imaging since only a single site is imaged (as opposed to a large field of many cells). For cells this indexing of cell positions enables much faster analysis than is currently available.

The system can be used with samples of single or multiple cells, molecules, compounds, organisms and biological and chemical media that adhere to the surfaces, as well as for samples that do not. Cavities or other entrapment devices can be used to position non-adherent samples.

The micro-patterned plate system advantageously solves the problem of positive selection of samples. The addressable array of removable pallets allows one to quickly and selectively remove samples from the plate for further processing. The use of removable pallets eliminates the need to cut around the sample, greatly increasing the speed and throughput while reducing the complexity for selecting samples. Since the pallets are arranged on a plate, high speed analysis and sample selection can be performed at rates comparable to flow cytometry in a far simpler manner.

In a preferred embodiment, as depicted in FIG. 1A, a plate 10 is manufactured in such a way that samples 14 such as single or multiple cells, micro-organisms, proteins, DNA, biomolecules and other biological media can be positioned at specific locations or sites 13 on the plate 10 for the purpose of performing addressable analyses on the samples 14. Some or all of the sites 13 are preferably built from a removable material in the form of pallets 12 so that a subset of the samples 14 of interest can be readily separated and isolated from the plate 10 for further processing or analysis. The plate can contain structures or chemical treatments that enhance or promote the attachment and/or function of the samples 14, and that promote or assist in their analyses. The plate 10 can also contain structures that aid in the coupling between the plate 10 and external instruments. The plate 10 can also contain additional structures that aid in accessory operations, such as maintaining proper chemical conditions for the samples.

Figure 1B:
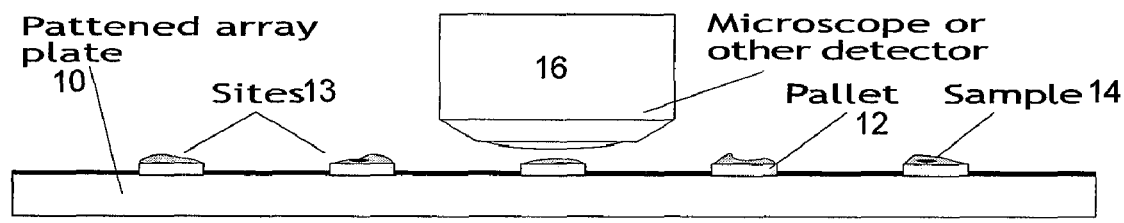
FIG. 1B is a side view of a micro-patterned plate with samples (cells) attached to pallets at specific addressable sites.

Referring to FIG. 1B, the micro-patterned plate 10, as depicted, includes samples 14 (such as single or multiple cells) attached to specific addressable sites 13, i.e., small, thin pallets 12 which adhere to the plate 10 at the sites 13. As depicted in this embodiment, a microscope or other detector 16 is used to image the samples 14 as the samples 14 are rapidly moved into position under the detector 16. Each site 13 can be imaged, or probed with light or other energy (e.g., magnetic, electrical, mechanical, thermal energy) to determine the properties of the samples 14 trapped at the site 13 or to modify the sample 14 at the site 13. Furthermore, the sites 13, actually pallets 12, containing samples 14 of interest can then be removed from the plate 10 for isolation from the plate 10 for further analysis or processing.

The pallets 12 are prepared on the surface of the plate 10 and preferably constructed from a second material having properties that differ from the bulk material of the plate 10. The pallets 12 can be removed from the supporting plate 10, carrying the sample 14 with it, by a variety of mechanisms so that samples 14 can be isolated and removed from the plate 10. The sites 13 or pallets 12 can be prepared by locally modifying the surface chemistry or by physically altering the surface. The sites 13 or pallets 12 are intended to be small enough to enable the entrapment of a few or single cells, micro-organisms, biomolecules or other biological or chemical media (herein called samples 14) at each site 13. The pallets 12 can also contain structures that assist in the movement or placement of the pallets 12 after removal from the plate 10.

A pallet 12 can be removed by any means appropriate. Example methods include mechanically pushing or lifting the pallet 12 from the plate 10, using localized heat or light to change the adhesion property of the pallet 12, using acoustical or mechanical shock to dislodge the pallet 12 from the plate 10, using high energy laser pulses to dislodge the pallet 12 from the plate 10, changing the electrical or magnetic properties of the pallet 12, and the like.

Figure 2:
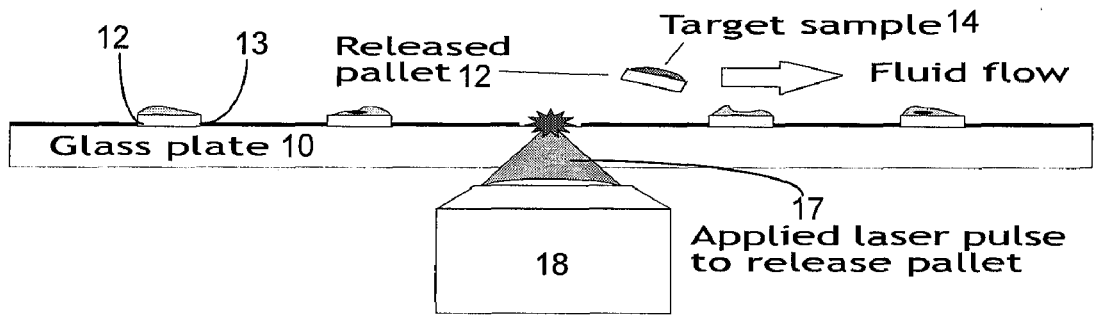
FIG. 2 is a side view of another embodiment of a micro-patterned plate and illustrates a positive selection of a sample by releasing the pallet containing the sample from the plate.

Turning to FIG. 2, an example of pallet removal using a laser pulse 17 from a laser 18 is shown. As illustrated, a positive selection of a sample 14 is accomplished by releasing the pallet 12 containing the sample 14 from the plate 10. As noted above, other methods of pallet release can be employed including the application of mechanical, electrical, thermal, optical, magnetic energy. The released pallet 12 can be flowed downstream for collection, or can be collected by other means (such as decanting or pipetting).

The sites 13 or pallets 12 are preferably formed close together so that the plate 10 can be moved under an analysis instrument to rapidly perform analysis of many sites 13. For example, if the sites 13 are positioned 0.1 mm apart, then the plate 10 can be moved at 50 mm/sec to analyze 500 samples per second. Samples 14 can be attached to the sites 13 in any of a number of methods. For example, living cells can be allowed to float in a medium until they attach to the sites. The remaining cells can be washed away leaving an addressable array of cells that can be rapidly imaged. Conventional methods such as spotting, silkscreening, stenciling, lithography, optical manipulation, or mechanical attachment can also be used to attach the samples to the sites.

Figure 6:
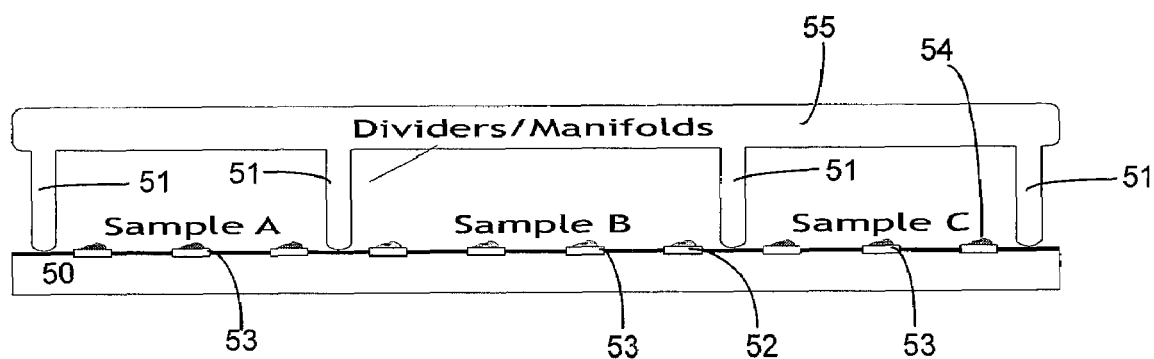
FIG. 6 is a side view of a plate showing the use of temporary or permanent dividers to allow samples of different types or histories to be plated on the plate at different locations or within different channels.

The sites 13 or pallets 12 can form rectangular or other regular patterns (e.g., hexagonal, circular, linear, etc.), or can be randomly oriented. The patterned sites or pallets can be positioned within a larger structure such as at the bottom of a multi-well plate. The patterned plate can allow other structures to be placed within it to facilitate other functions, for example the use of temporary dividers that allow different samples to be introduced into different regions of the plate, or fluidic structures (e.g., channels) to facilitate the flow of buffer across the sites (as illustrated in FIG. 6).

Figure 3:
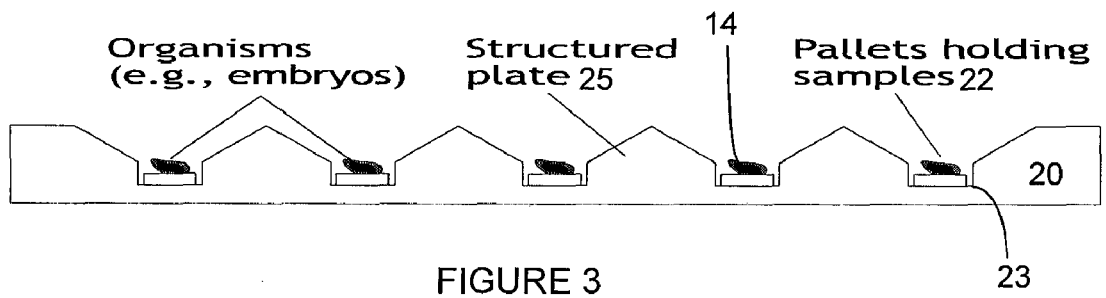
FIG. 3 is a side view of another embodiment of a micro-patterned plate with samples (organisms) attached to specific addressable sites.

Referring to FIG. 3, a micro-patterned plate 20 is shown with samples 14 attached to specific addressable sites 23. In this embodiment, a 3-D structured pattern 25 on the plate 20 assists in the collection of the sample 24 at the specific sites, where they can be attached directly to the plate 20 or to small pallets 22 at each site 23.

The physical shape of the surface can be modified to enhance the capture at sites (and not at non-sites), or to improve the analysis. For example, the sites (see 32, FIG. 4) can be formed on top of posts. This provides the advantage that non-sites are out of focus (see 35, FIG. 4) for a microscopy imaging system, reducing background in the image. Other examples can include cavities that trap samples within them, or opaque regions on the plate.

Other features can be added to the plate to facilitate its coupling to an external instrument. For example, optical encoders, electrodes, or magnetic devices can be included on the plate to facilitate placement; sensors can be used to test for growth conditions; fiducial marks can be included for optical alignment; etc.

Figure 4:
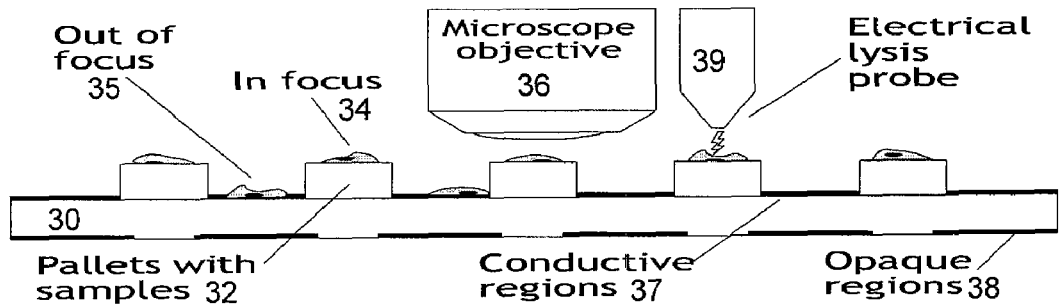
FIG. 4 is a side view of another embodiment of a micro-patterned plate with samples (cells) attached to specific addressable sites.

Some of the noted enhancements are shown in FIG. 4. As depicted in FIG. 4, a micro-patterned plate 30 includes samples (cells) 34 attached to pallets 32 or posts at specific addressable sites. In this embodiment, a microscope objective 36 is used to image the "in focus" samples 34 as they are rapidly moved into position under the objective 36. Other included features include patterned electrodes 37, patterned opaque regions 38, and externally applied electrical fields 39 that can be used to lyse specific cells of interest.

The chemical property of the sites can also be modified to enhance the capture at the sites (and not at non-sites), or to improve the analysis. For example, surface chemistry can be modified to make some regions hydrophobic and other hydrophilic to enhance cell adhesion at the hydrophobic sites. Surface chemistry can also be used to make a non-site of the plate opaque and site-regions transparent to provide local apertures for enhanced optical imaging.

Figure 5:
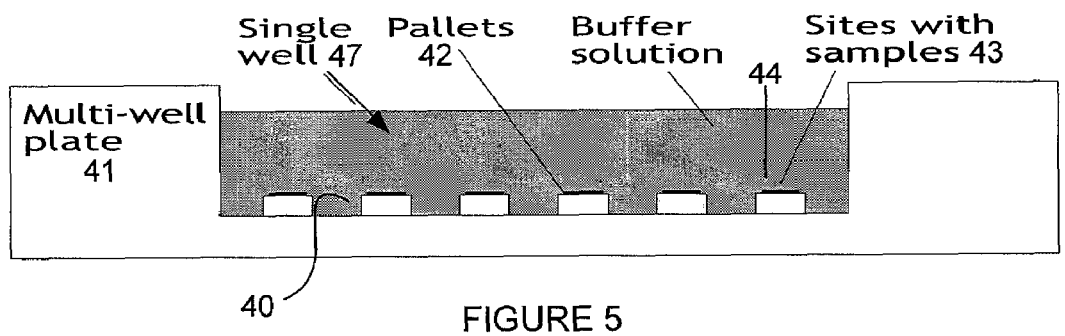
FIG. 5 is a side view of another embodiment of a micro-patterned plate placed at the bottom of a single well of a multiwell plate, allowing conventional tools to be used with the plate.

The array of sites can be produced within existing industry standard trays and cassettes. For example, the sites can be fabricated within the bottoms of multi-well plates, providing high speed addressable assays to industry standard equipment (see, e.g., FIG. 5). The array of sites can also be produced within a customized system of cartridges(see, e.g., FIG. 6).

As depicted in FIG. 6, a micro-patterned plate 50 is shown to include temporary or permanent dividers 51 attached to a fluidic cap 55 to allow samples 54 of different types or histories to be plated on the plate 50 at different locations 53. This allows multiplexed analysis to be done on a single plate. The dividing structures 51 can also facilitate the flow of buffers over the sample regions for extraction of released pallets 52.

Figure 7A:
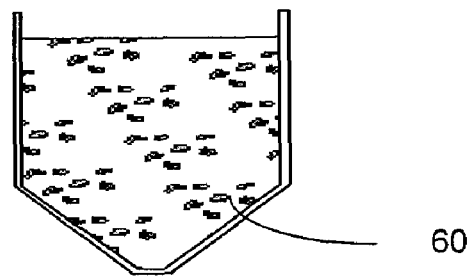
FIGS. 7A and 7B show steps in a process using a pallet plate for adherent cell screening and culturing.
Figure 7A:
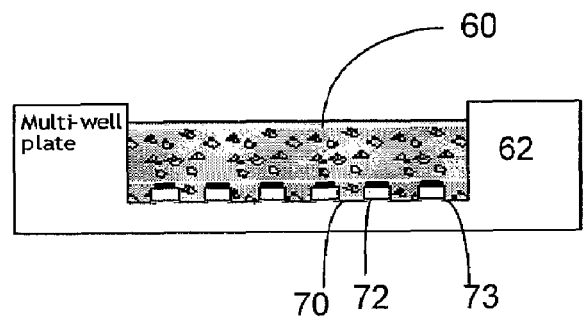
Figure 7A:
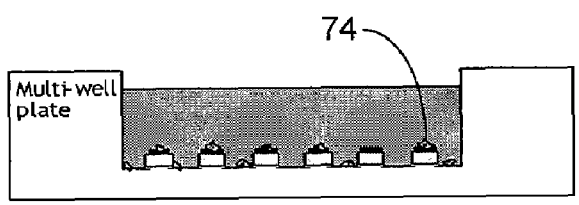
Figure 7A:
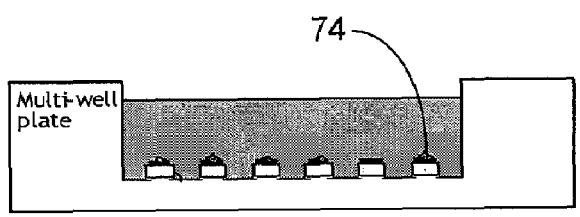
Figure 7B:
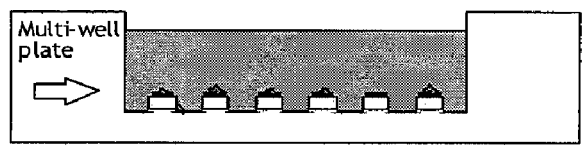
Figure 7B:
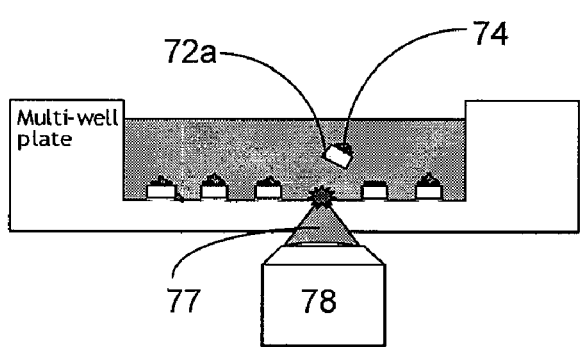
Figure 7B:
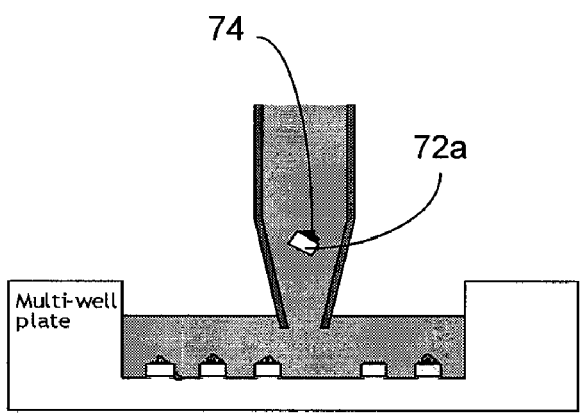
Figure 7B:
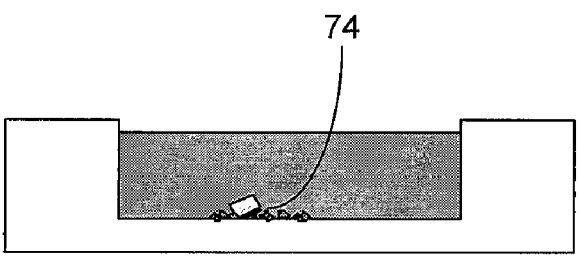

Turning to FIGS. 7A and 7B, steps in a process using a pallet plate for adherent cell screening and culturing are shown. This example illustrates how the disclosed system can be used to screen for rare cells or cells of interest from a large collection of cells. For example, the adherent cells can be taken from a patient biopsy and the disclosed system can be used to search for and select cells that show unusual or malignant behavior. Or adherent cells might be treated with a DNA vector in hopes of transfecting the cells, and the system used to find and isolate the cells that were properly transfected.

In accordance with the example process, cells 60 are pretreated, at step 1, according to an appropriate protocol, the cells 60 are then dispersed, at step 2, over the plate 70 and allowed to attach to the plate 70 or the pallet 72 at a plurality of sites 73. This can be done in a multi-well plate 62, as shown, or a single well plate. The cells adhere, as a sample 74, at step 3, to the plate 70 or pallet 72. Since the plate is treated and patterned, cells prefer to adhere at specific sites. At step 4, the plate is then preferably washed and further assay work is preferably performed to label the cells of interest. The plate is screened by detector 76, at step 5, to gain statistical information about the cell population and to identify cells of interest. Pallets 72a containing the cells of interest are (sample 74) dislodged (released), at step 6, from the plate, preferably, e.g., by a high energy laser pulse 77 from a laser 78. The free floating pallets 72a are then collected, at step 7, from the buffer solution. At step 8, new cell cultures are grown from the released cells 74.

Figure 8A:
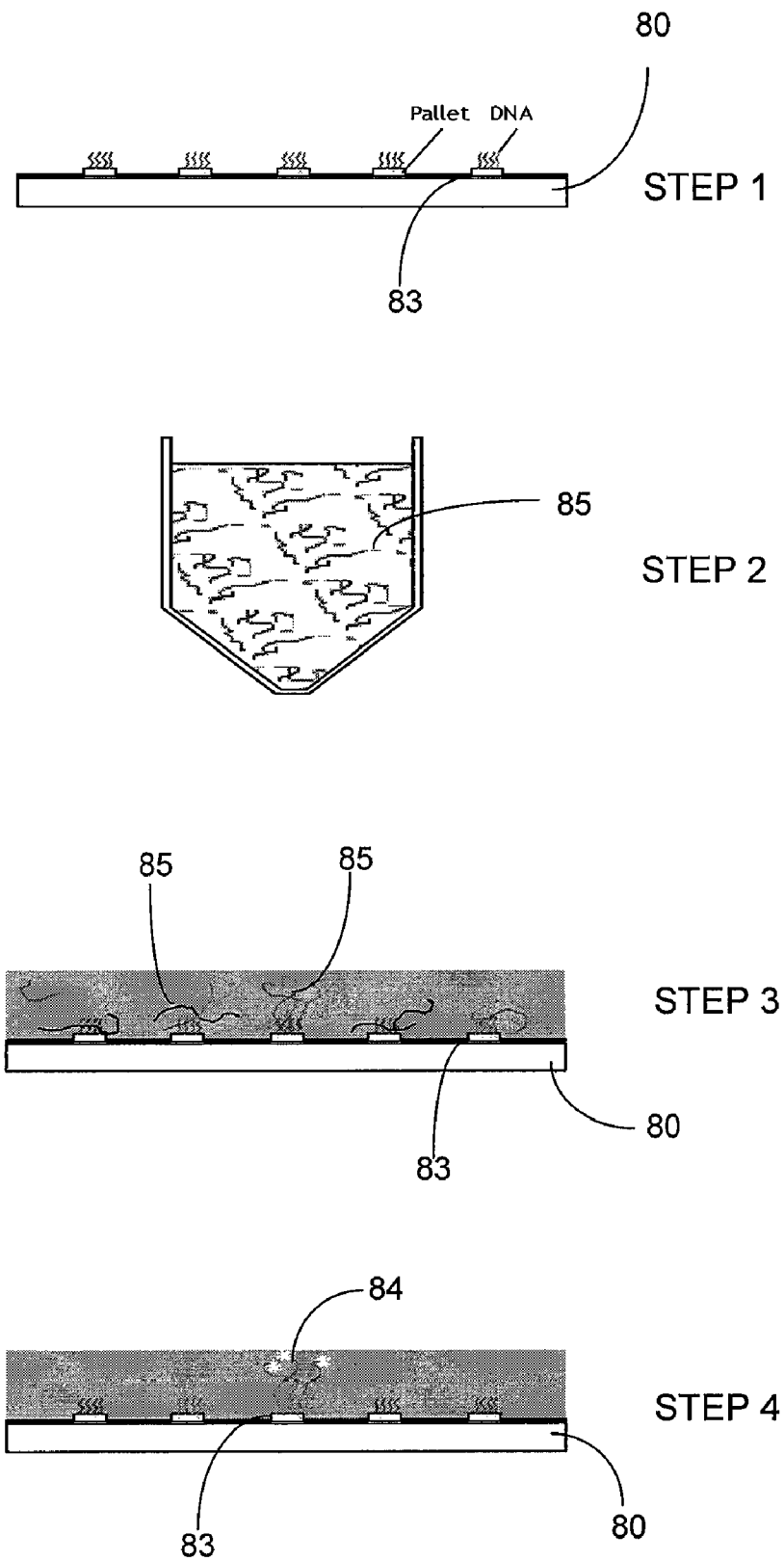
FIGS. 8A and 8B show steps in a process using a pallet plate for DNA screening.
Figure 8B:
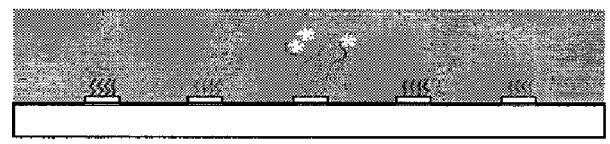
Figure 8B:
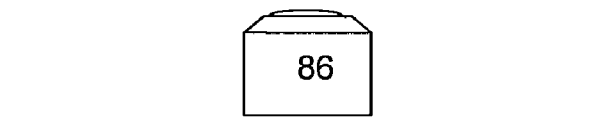
Figure 8B:
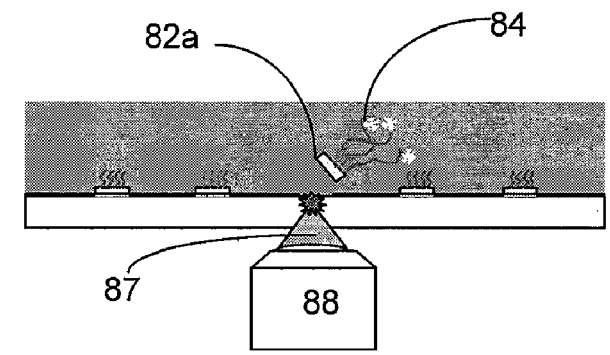
Figure 8B:
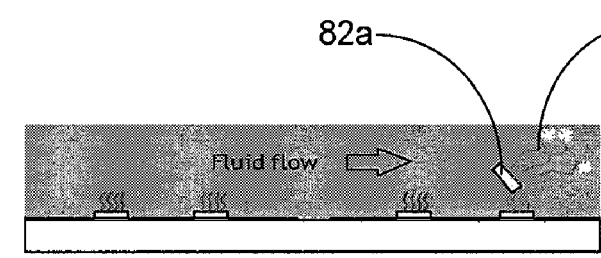
Figure 8B:
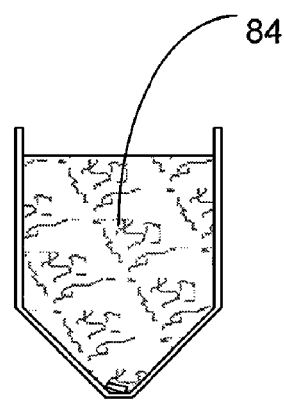

Turning now to FIGS. 8A and 8B, steps in a process using a pallet plate for DNA screening are shown. This example illustrates how the disclosed system can be used to screen for rare DNA strands from a large collection of DNA. For example, an unknown disease causing agent can be screened against a DNA plate to select strands of interest. Then the strands of interest can be isolated and PCR performed to amplify them for further analysis. The steps of the process are as follows: At step 1, a plate 80 is spotted with oligonucleotides at specific sites 83 which act as targets for DNA strands. The oligos are also prepared to act as controls. At step 2, DNA 85 is taken from sample, denatured and pretreated according to an appropriate protocol. At step 3, DNA 85 is dispersed over the plate 80 and allowed to hybridize to their matching targets at specific sites 83. At step 4, the plate is thoroughly washed to remove unbound DNA. Further assay work is performed to label the DNA of interest. The plate is then screened by the detector 86, at step 5, for statistical analysis of the sample and to identify DNA of interest. The pallets 82a containing the DNA of interest 84 are dislodged (released), at step 6, from the plate 80 by a high energy laser pulse 87 from a laser 88. At step 7, the free floating pallets are collected from the buffer solution. At step 8, DNA 84 is denatured from the pallet and used in PCR reaction to amplify the sample.

Figure 9:
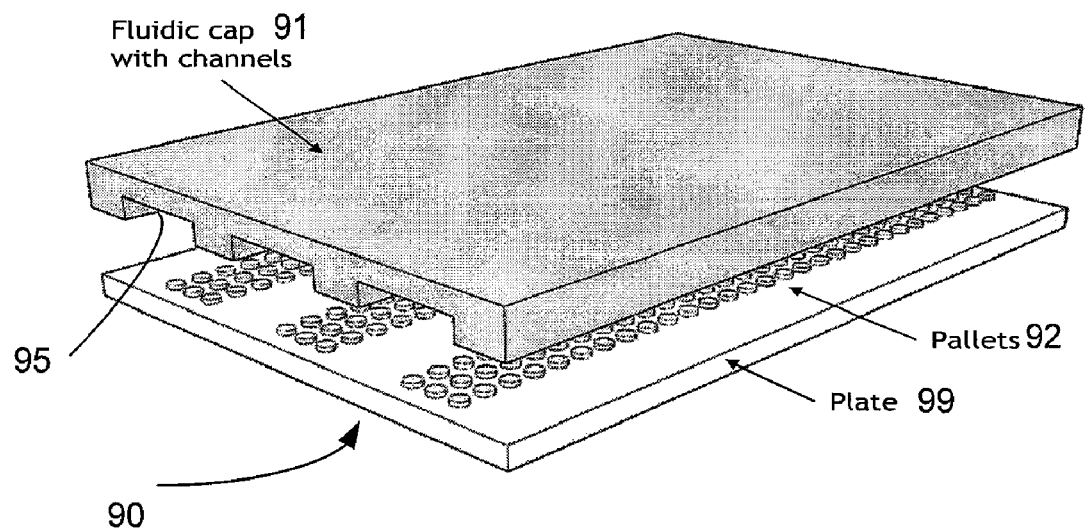
FIG. 9 is a perspective view of an integrated pallet plate cassette for automated assays.

Referring to FIG. 9, an integrated pallet plate cassette 90 for automated assays is illustrated. This example illustrates how the disclosed system can be integrated into other systems to produce an automated cartridge system. As depicted in FIG. 9, the integrated pallet plate cassette 90 includes a micropallet plate 99 with a plurality of pallets 92 formed in three arrays on the plate 99, and a fluidic cap 91 with small channels 95 formed on its underside. The cap 91 mates with the micropallet plate 99 to flow buffers over the pallets 92.

Turning to FIGS. 10A through M, a process using a micro-machined integrated pallet plate cassette 100 is shown. The cassette 100 includes a pallet plate 109 that preferably includes a pre-set array of releasable pallets 102 for cell culturing that are releasably positioned atop of the plate 109 formed of glass or the like. The pallets 102 are preferably treated to promote cell growth at the center of the pallets 102. The pallets 102 are preferably indexed, e.g., bar coded, so that their positions are known in advance of use of the cassette 100.

In FIGS. 10B and 10C, the cap 101 is closed on to the plate 109 revealing an access hole 107. In FIG. 10D cells are dispersed over the plate 109 and allowed to attach to the plate at specific sites 102 or pallets. The plate 109 is then screened by the detector 106, as depicted in FIG. 10E, for statistical analysis of the sample and to identify cells of interest. A pallet 102a containing the cells of interest is dislodged (released), as shown in FIG. 10F, from the plate 109 by a high energy laser pulse from a laser 108. As shown in FIG. 10G, the free floating pallet 102a is collected from the buffer solution toward the end of the plate 109. In FIG. 10H, a second pallet 102b containing additional cells of interest is dislodged (released) from the plate 109 by a high energy laser pulse from a laser 108. As shown in FIG. 10I, the free floating pallet 102b is collected from the buffer solution toward the end of the plate 109. As depicted in FIGS. 10J and 10K, the pallets 102a and 102b are extracted through access hole 107 using an extractor 110. New cell cultures are grown from the released cells, as shown in FIGS. 10L and 10M.

Figure 11:
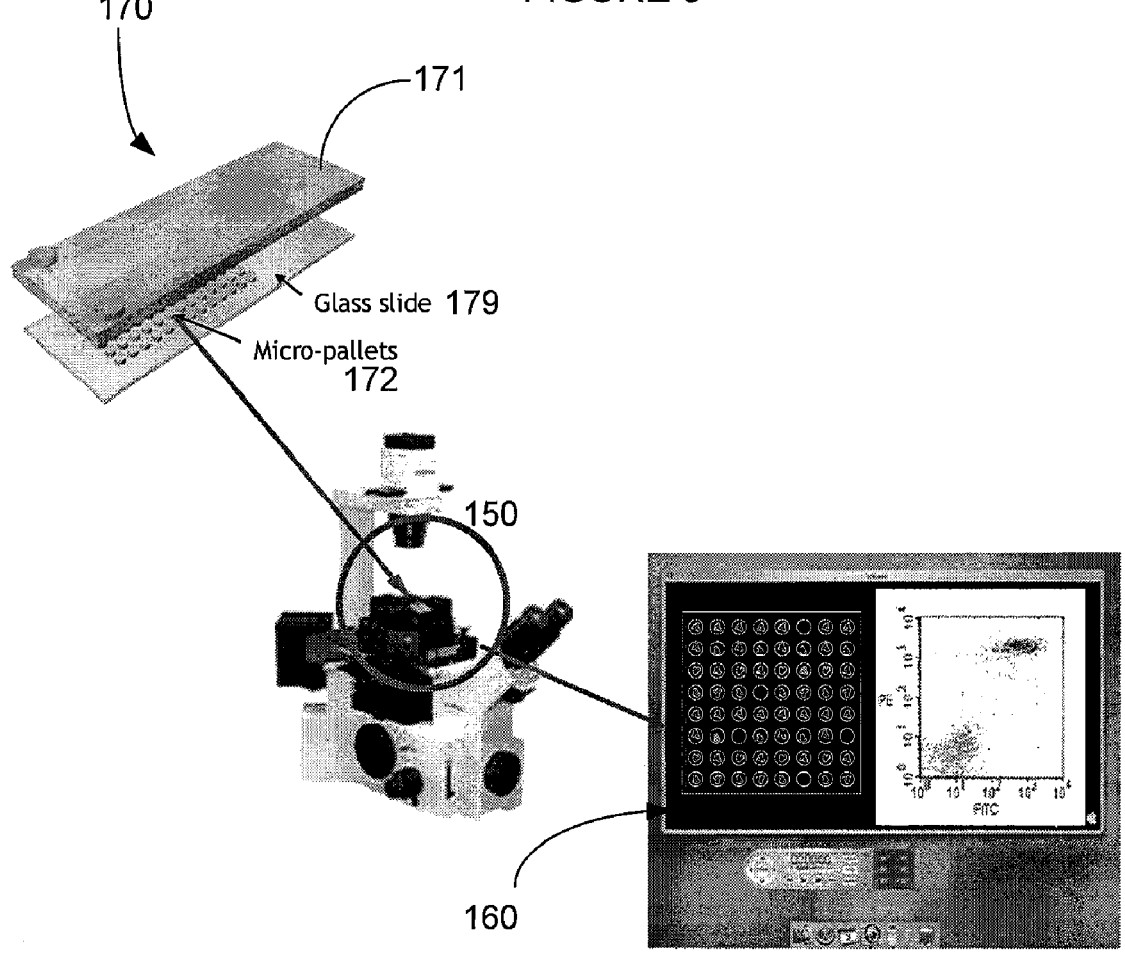
FIG. 11 is a schematic of a high content screening and cell selection system utilizing a micro-pallet cassette comprising an array of micro-pallets.

As shown in FIG. 11, a cassette 170 comprising a substrate or plate 179 formed of glass or the like and a cap 171. The plate 179 can include an array of micro-pallets 172—e.g., providing 500,000 (50×50 microns) pallet sites—positioned on the plate 179. The cassette 170 can be used with a microscope attachment 150 for imaging, fluorescent analysis, sorting, and the like. Analysis software provided on a computer 160 can be used for high content screening and cell selection. A pallet extractor can be used to extract a selected pallet from the cassette 170.

The micro-pallet array system described herein advantageously enables the use of broad selection criteria for single cells, cell colonies and organisms. The system advantageously enables the analysis of cells or other materials residing on the pallets for a variety of properties, followed by positive selection of cells while the cells remain adherent to the pallets. Depending on the method of analysis, these properties or selection criteria can include optical properties such as fluorescence, light scatter, morphology, colony formation and other biological properties, chemical properties, and mechanical properties. For example, early detection of cells based on the analysis of the fluorescence of those cells expressing a target gene encoding a fluorescent protein followed by cell selection, i.e., pallet release and collection, will enable rapid establishment of clonal populations. Significant savings in time and manpower compared to selection with a toxic antibiotic is possible as a result.

The pallet release and collection process of the micro-pallet array system subjects the cells to less perturbation than sorting by flow cytometry, since the cells remain adherent during both analysis and sorting. Improved cell health and viability is provided as a result. Moreover, cells grown on the pallets will display their full set of cell-surface proteins as well as retain their native morphology and signaling properties. Thus, a broader set of cell attributes are available for use as selection criteria. Importantly, these properties can be analyzed over time to enable selection based on the temporal change of a particular property.

Use of the micro-pallet array system advantageously enables the selection and sorting of cells based on dynamic phenomena such as protein translocation, kinase activation, ionic changes and the like. In conventional methods, when a single cell or group of cells is isolated from a mixed population, the selection is almost always based on a property of the cell that does not change over the time of the selection process, e.g., the presence of a surface protein or the expression of a fluorescent protein. The lifetimes of these proteins is on the scale of many hours to days and longer so that the amount of a cell's protein is the same before, during, and after the sorting process. However, many cellular properties change on much more rapid time scales (seconds to minutes). For example, the intracellular free calcium concentration or the organization of the cytoskeletal network. Properties such as these can be very dynamic in cells especially in response to the addition of a stimuli or drugs to the cellular environment. Since cells behave asynchronously in response to an agonist or inhibitor, these dynamic properties are most easily assessed when measured over time, i.e. before, during, and after addition of a stimulus or drug.

Isolation or the selection of cells on the basis of dynamic properties has not generally been possible since these attributes are in a state of flux faster than the time scales of available or conventional sorting methods. In addition, as alluded to above, detaching the adherent cells from a surface for sorting eliminates or at the very least dramatically alters these dynamic cell processes. Lastly, many conventional sorting processes, such as flow cytometry, permit only a single time point measurement; consequently, changes rapidly occurring within a single cell are very difficult to use as a selection criterion. A method that allowed adherent cells to be selected and isolated based on dynamic properties would significantly extend the characteristics on which sorting could be based. For example, cells could be selected based on their ability to respond to an agonist or the inhibition of a response by an antagonist. By combining sophisticated imaging technologies, such as standard imaging cytometry or state-of-the-art imaging technology such as laser scanning cytometry, with the releasable micro-pallets array system, sorting based on differences in cellular behaviors or signaling dynamics is possible.

By virtue of the ability to follow cells over time, i.e., follow the encoded or addressable pallets over time, more complex screening criteria can be used. One such application is the screening and selecting cells expressing a genetically encoded protein whose properties change over time, for example fluorescent protein conjugates whose fluorescence properties increased or decreased after cellular stimulation. Cells could be selected based on the minimal and maximal fluorescence change after stimulation to produce a cell line showing enhanced dynamic range of the fluorescence property. Another example is the screening of random siRNA libraries for proteins that block cytoplasmic translocation of a second protein or that diminish the frequency of calcium spiking in cells. Transfected cells can be surveyed over time while on the pallet arrays for these dynamic alterations in signaling. The positive cells can then be released, cultured and the siRNA sequence in that cell decoded.

The advantages the micro-pallet array system poses are also applicable to stem cell selection technology. Most stem cell isolations rely on one or more biomarkers (usually a surface antigen). Sorting of adherent stem cells will improve detection and broaden selection of surface markers by allowing replenishment of surface proteins after the disaggregation step. As a result, small numbers of stem cells or their progeny can be rapidly identified in a mass population and directly isolated in one step.

By virtue of the ability to follow individual cells over time, cloning of cells possessing particular temporal characteristics can be performed. This ability enables screening and selecting cells genetically engineered to express encoded proteins designed to indicate changes in intracellular states. These states include a variety of cellular properties such as activity of enzymes, concentrations of ions or second messengers, pH, enzyme activity, protein location or any other property that may vary with time. A current practice for generating improved indicators involves generating a large number of different DNA molecules by random mutagenesis of the gene encoding a prototype indicator. These various DNA sequences are used to transfect cells followed by screening of the cells after inducing the desired change of cellular state. Since current techniques enable individual cells to be measured at only a single point in time, the magnitude of the change in the indicator cannot be determined. In identifying cells expressing the best choice of indicator, cells must be selected based on the extent of change (i.e. dynamic range) of the indicator. The most desirable cells show the greatest change in the indicator as the cell's state changes. For example, the ideal indicator of intracellular calcium concentration which has been designed to vary its fluorescence resonance energy transfer (FRET) based on binding of calcium will exhibit the greatest dynamic range in FRET as the calcium increases from minimal to maximal values. Cells chosen only on the basis of a high degree of FRET after raising intracellular calcium may not be desirable if their basal FRET was also high. The ability to select and collect cells possessing indicators with the greatest dynamic range is a tremendous advance in this application.

Another area of need for temporal measurements in cell cloning is the generation of cell lines with homogeneous signaling properties. Many cell-based screening assays rely on time-resolved readouts such as translocation of tagged molecules, changes in the fluorescence properties of intracellular indicators or other dynamic markers of cell state. The end goal is to determine if the state of the cell has been perturbed by an experimental manipulation such as exposure to a drug, to small interfering RNA, or other modality. A complication in the analysis of these assays is the heterogeneity among individual cells in their response to a stimulus over time. An example of this goal is the pattern of translocation of a fluorescently-tagged signaling protein after stimulation of the cell with an agonist. Within a given population, individual cells exposed to the same stimulus can display very different patterns of translocation. Assays relying on such readouts would be improved by the clonal generation of cells possessing homogeneous temporal properties, such as identical patterns of translocation after a defined stimulus. The homogeneity of such cell lines could be enhanced by screening cells based on measurements at two or more points in time followed by selection and isolation of individual cells with the desired response pattern. These cells could then be clonally expanded to give a population of cells with more consistent behavior.

Figure 12:
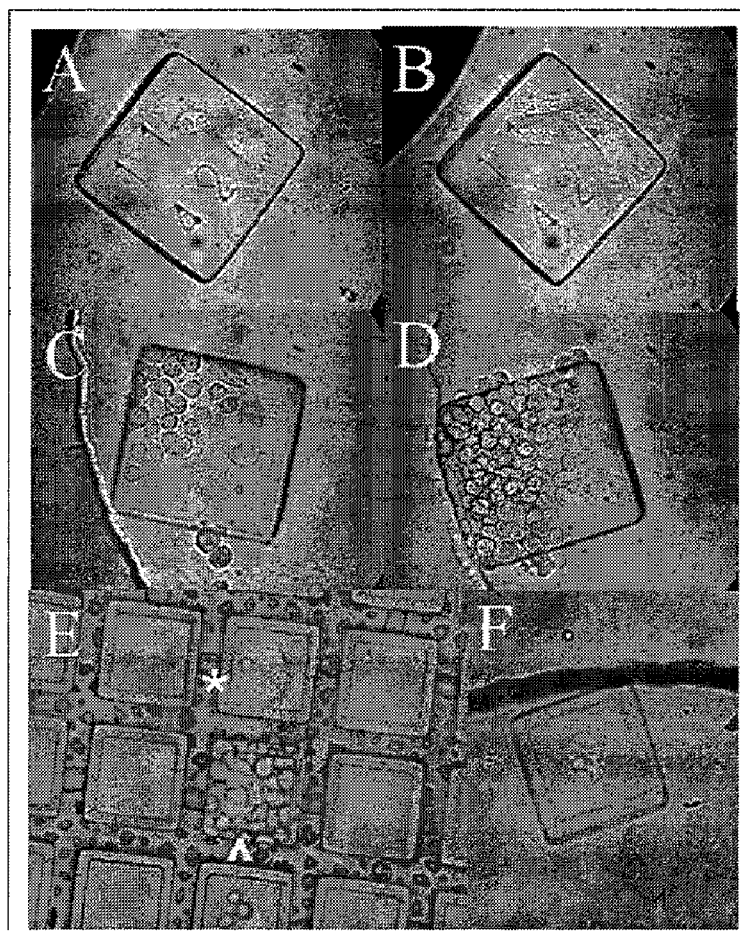
FIGS. 12A through 12F are images showing the identification and collection of biological cells based on differing cellular characteristics.

Turning to FIG. 12, an experiment demonstrating the cell selection based on temporal properties is describe. For this experiment and others described herein, arrays of pallets on glass slides were fabricated using standard photolithography, i.e., SU-8 films of the desired thickness were obtained by spin-coating and baking the resist on glass slides followed by exposing the SU-8 film to UV light through a photomask possessing the design features. The SU-8 samples were developed and dried by a nitrogen stream. After fabrication, the pallet array was treated to form a hydrophobic perfluoroalkylsilane layer on the silicone oxide surface. This step enables the array to retain a continuous air bubble ("virtual wall") between the pallets that prevents access of solutions or cells in the region between the pallets. (See, e.g., U.S. patent application Ser. No. 11/539695, filed Oct. 9, 2006, titled Micro-Bubble Plate For Patterning Biological And Non-Biological Materials, which application is incorporated herein by reference.) After silanization, a chamber was constructed by using PDMS to attach a silicon "O"-ring (24 mm outer diameter) to the pallet array. The top surfaces of pallets were then modified using collagen or fibronectin to enhance cell adhesion. Arrays were washed with media prior to plating of cells.

To collect released pallets and adhered cells, microwell plates was fabricated by casting PDMS against SU-8 molds. The plates possessed multiple square or round wells with dimensions of 1 mm. The wells were 150 µm in depth and separated by walls 0.25 mm thick. Each well was numerically labeled for identification. The microwell plates were circular with a diameter of 17 mm and was designed to mate with the chamber containing the pallet array to form a water-tight seal. Before pallet release a PDMS microwell plate was sealed to the pallet array using a sterile gasket. After pallet release, the microwell plate-pallet array unit was inverted so that the pallets and aqueous solution settled into the microwell plate by gravity.

As noted above, an asset of the pallet-array system is the ability to select cells based on dynamic phenomena in which multiple measurements are required from the same cell or group of cells over time. To demonstrate the utility of the pallet array in separations based on temporal properties, cells were separated based on their rate of growth. HeLa cells were plated on an array with numerically encoded pallets at a density yielding <1 cell per pallet and examined by microscopy within two hours to verify that the pallets possessed either 0 or 1 cell per pallet. In these experiments, pallets were encoded with a unique numerical code to enable specific pallets to be followed on the array over several days. Pallets that contained single cells at the time of plating were again examined at 96 hours of culture. Pallets with colonies of <4 cells (2.5 ±0.8 cells [average±standard deviation], n=6) at this time point were detached, collected into a first multi-well plate, and cultured in conditioned media. As seen in the FIG. 12A, the number of cells in each colony derived from a single cell was easily determined. Pallets with ≧22 cells (25±2, n=5) at 96 hours were also released, collected into a second multi-well plate, and placed in conditioned media (see FIG. 12C). The number of cells present for each collected pallet was again determined at 118 and 144 hours after plating on the pallet array. At 144 hours, the wells with the slowly and rapidly growing populations possessed 3.0±1.6 vs. 65±18 cells, respectively (see FIGS. 12B and 12D). A fit of the growth curves of the two cell populations yielded a doubling time of 4 days for the slowly growing cells and 1 day for the faster growing cells, thus demonstrating successful sorting on the basis of doubling time or growth rate. These data also demonstrate the ability to collect colonies of cells. Selections based on growth rate may find utility in the identification of genes and proteins involved in modulating the cell cycle or promoting growth inhibition. Other types of separations enabled by repeated measurements on a single cell include selections based on temporal patterns of ion concentrations (e.g. calcium), protein translocation, enzyme activation (e.g. kinases), or cytoskeletal alterations.

Turning to FIGS. 12E and 12F, an experiment demonstrating the cell selection based on cell morphology is described. Flow cytometry can be used to assess gross cellular morphology such as size and granularity based on forward light scatter. Recent advances in high-speed imaging of cells in a flow cell have proven useful in acquiring additional structural data that might prove useful for increasing potential sort decisions. Nonetheless, these approaches require cells to be put into suspension prior to the analysis resulting in loss of the characteristic three-dimensional structure of cells in their adherent state. To demonstrate cell separation by morphology, HeLa cells were plated on a pallet array at a density yielding <1 cell per pallet and cultured for 4 days. HeLa cells are known to display a number of morphologies under standard tissue culture conditions. When viewed under transillumination, occasional cells on the pallets possessed a well-spread phenotype that was preserved as the cells were maintained in culture on the array (FIG. 12E). More commonly seen were cells displaying a more spherical morphology with minimal pallet contact (FIG. 12E). The "*" marks the very flattened round cells while the "^" marks the spherical cells. Pallets containing cells exhibiting the two morphologies (n=6 of each phenotype) were released and collected in the same experiment. Upon sorting into a multi-well plate, the pallets were reexamined and all cells on the collected pallets retained their pre-release morphology even after continued culture for 3 days (FIG. 12F). Thus, the cells can be selected and collected based on their morphology or shape. Selections based on morphology may enable the identification of genes and/or proteins that modulate the cytoskeleton, surface attachment, or cell-to-cell adhesiveness.

Figure 13:
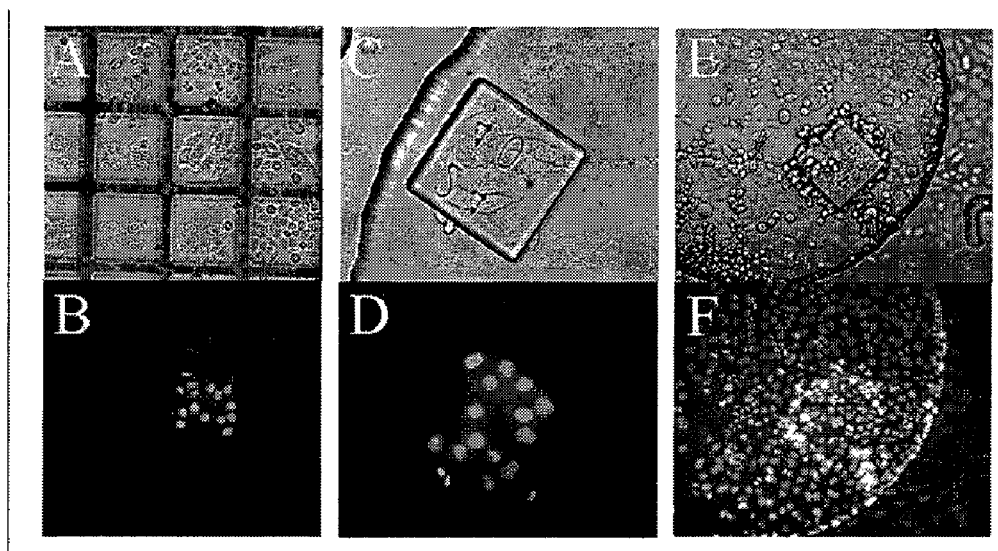

Turning to FIG. 13, an experiment demonstrating the cell selection based on the properties of individual cells in a clonal colony is described. Pallets in the arrays can be fabricated in a large range of sizes (tens to hundreds of microns). As discussed previously, either single cells or colonies of cells can be separated using this system. When single cells are cultured on pallets capable of accommodating multiple cells, colonies of cells form on the pallets. Since the virtual walls between the pallets restrict the movement of cells to other pallets, the majority of these colonies should be clonal in nature. Since the pallets can be repeatedly interrogated over time, the properties of the individual cells in a colony on a pallet can be measured as the colony grows. Thus, separations based on the traits of the descendents of a founder cell such as gene expression should be possible. For these studies, a HeLa cell line stably transfected with a protein composed of EGFP fused to the histone-H1 protein was used. Histone-H1 is tightly associated with cellular DNA so that transfected cells display green fluorescence localized to their nuclei. Wild-type HeLa cells were mixed with the EGFP-histone-H1 expressing cells at a ratio of 10:1, respectively. The cells were then plated on an array (175 µm sides, 40 µm gap, 50 µm height) at limiting dilution to yield <1 cell per pallet. The 5,600 pallets in the array were individually coded with a unique number to enable specific pallets to be followed before and after sorting. The pallet array was monitored by microscopy (transmitted light and fluorescence) over several days and the fluorescence of the progeny of each parental cell on the array was measured. Pallets with fluorescent cells were easily visualized amongst pallets containing nonfluorescent cells (FIGS. 13A and 13B). Under these conditions, the green autofluorescence of the pallets was not visible. After 72 hours of culture, 76% of the pallets possessed no cells, 22% contained colonies of nonfluorescent cells, and 2% displayed colonies with fluorescent cells (n=10 experiments). Colonies in which all cells expressed EGFP-histone-H1 possessed an average of 7+4 cells descended from the single parental cell originally cultured on the pallet. To demonstrate sorting of these clonal colonies, fluorescent colonies were released, collected, and placed in culture (FIGS. 13C and 13D). Expansion of these fluorescent colonies for six days yielded clonal populations of cells expressing the fusion protein (n=15) (FIG. 13E and 13F). These experiments demonstrate the ability to sort colonies of cells based on whether the individual cells retain the properties of the parental cell. This selection strategy may find utility in the molecular engineering of cells or the development of cell lines, for example stem cells.

Figure 14:
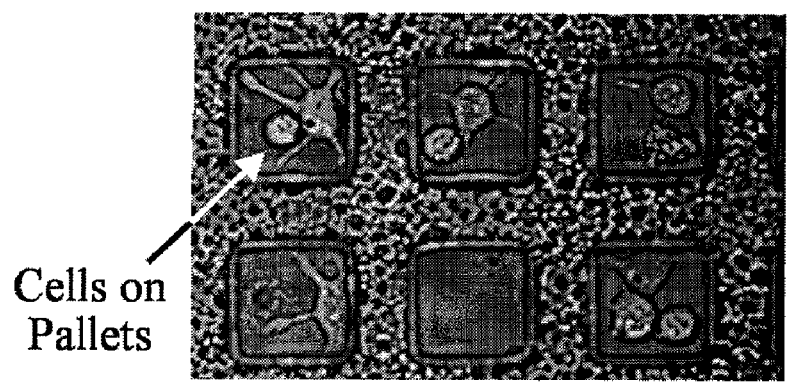
FIG. 14 is the transmitted light and corresponding fluorescence images of living cells stained with a long wavelength fluorescent dye (Alexa Fluor 647).

Standard selection criteria such as that used in flow cytometry, LCM, Palm System, antibiotic selection, and limiting dilution is also possible with the micro-pallet array system technology. These selection criteria include fluorescence such as that from autofluorescence, fluorescent molecules expressed by the cell, fluorescent dyes, immunofluorescence; fluorescence properties such as fluorescence lifetime, polarization, anisotropy, fluorescence resonance energy transfer, quenching, fluorescence spectra; bioluminescence; chemical staining; generation of colored products from chromogenic substrates; optical properties including light scattering, extinction, interference, phase, spectrophotometric absorption, polarization, infrared spectra; electrical properties including impedance and capacitance; acoustic properties; and others. For example, as shown in FIG. 14, cells stained using immunofluorescence can be analyzed and then be selected based on the absence, presence, or intensity of the surface protein. This example demonstrates that immunofluorescence staining can be performed on cells grown on pallets and cells can be visualized based on fluorescence staining of a cell-surface marker while cells are cultured on pallets. In this example, RBL cells were incubated with Alexa Fluor 647-labeled IgE (10 µg/mL) and then washed. RBL cells possess surface Fcε receptors which bind IgE. The Alexa Fluor-stained cells were easily visualized on the pallet array (ex/em-650/665 nm). An empty pallet (bottom row in center) shows no apparent background fluorescence.

Figure 10:
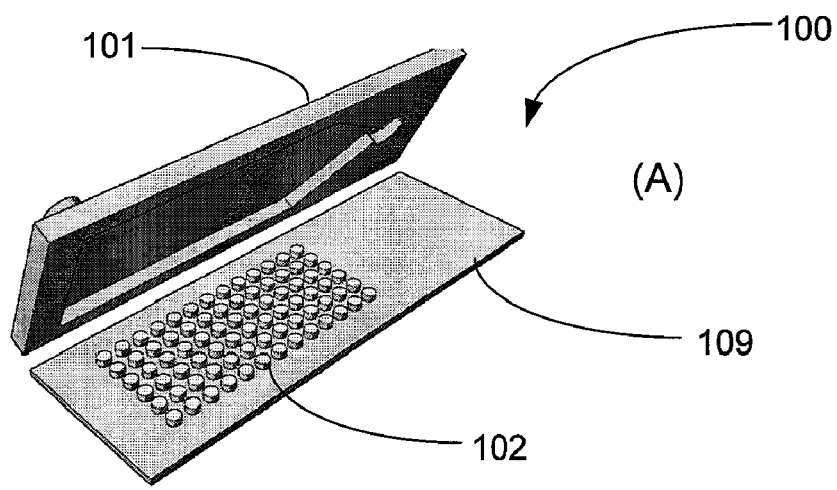
FIGS. 10A through M show steps in a process using an integrated pallet plate cassette for sample screening and culturing.
Figure 10:
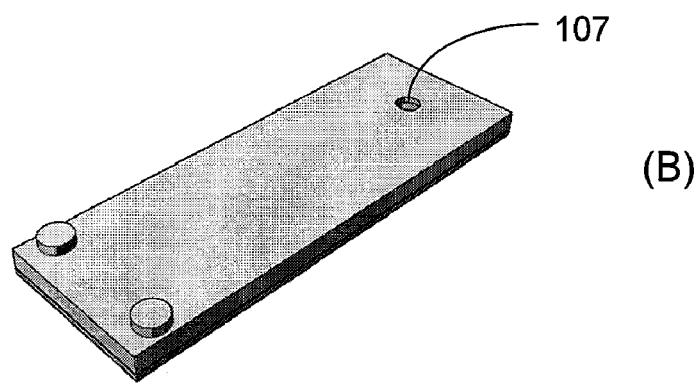
Figure 10:
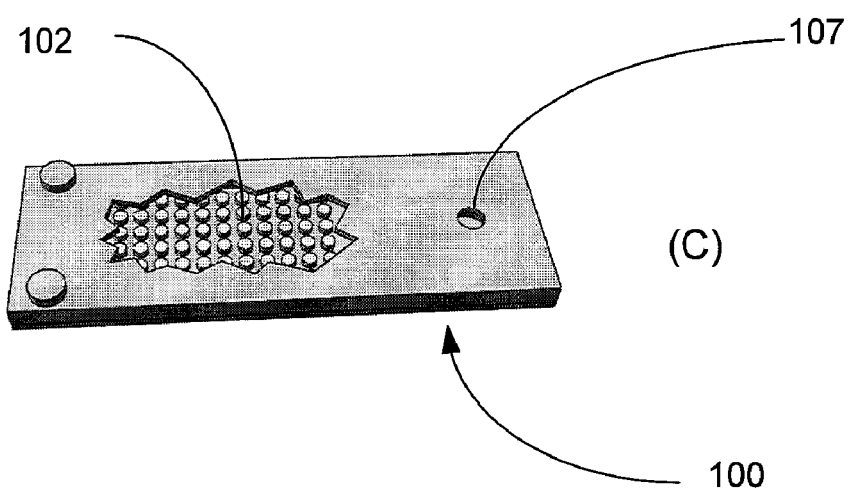
Figure 10:
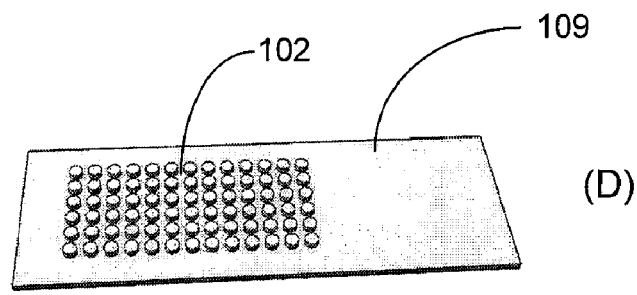
Figure 10:
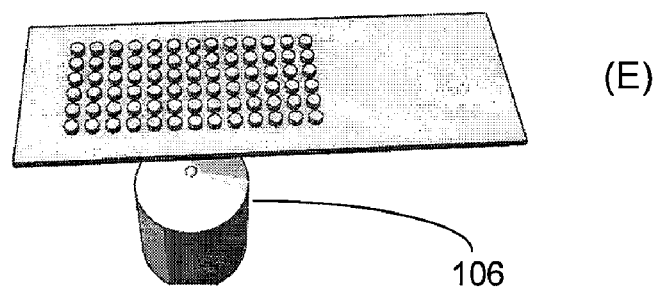
Figure 10:
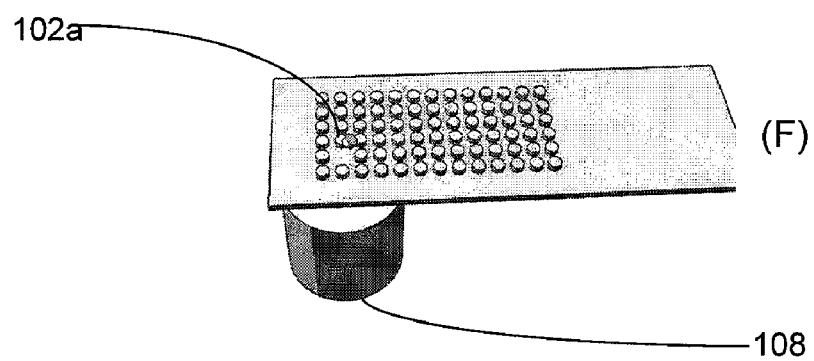
Figure 10:
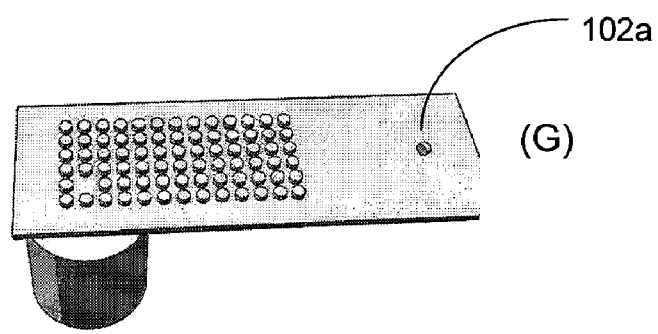
Figure 10:
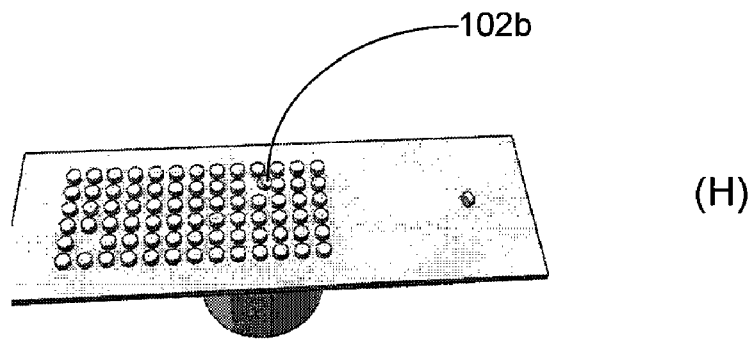
Figure 10:
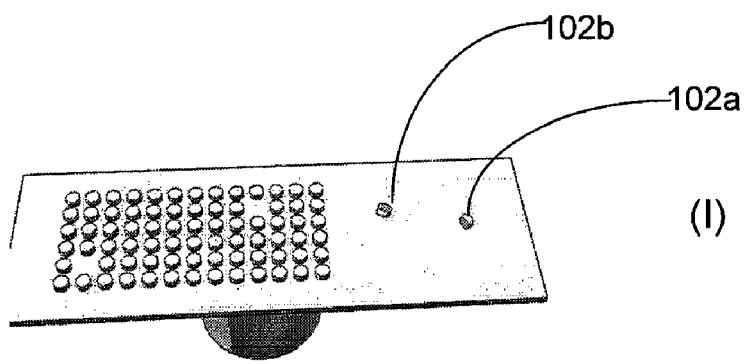
Figure 10:
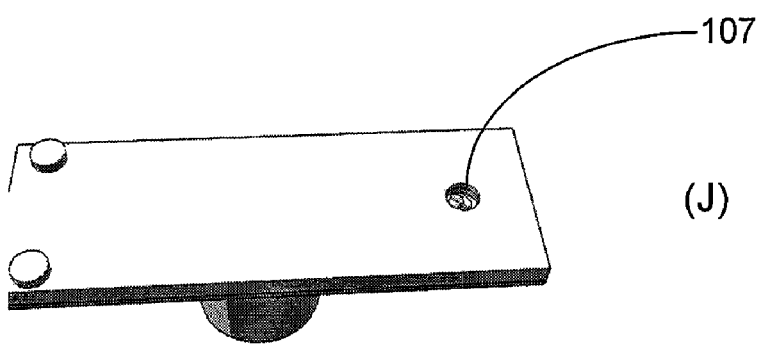
Figure 10:
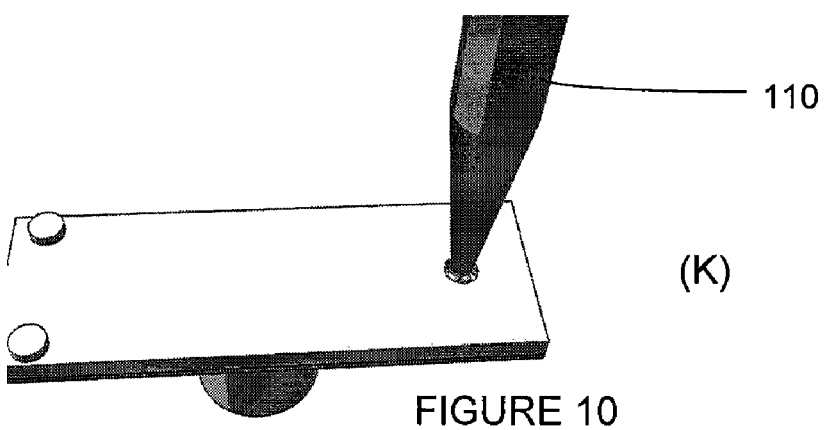
Figure 10:
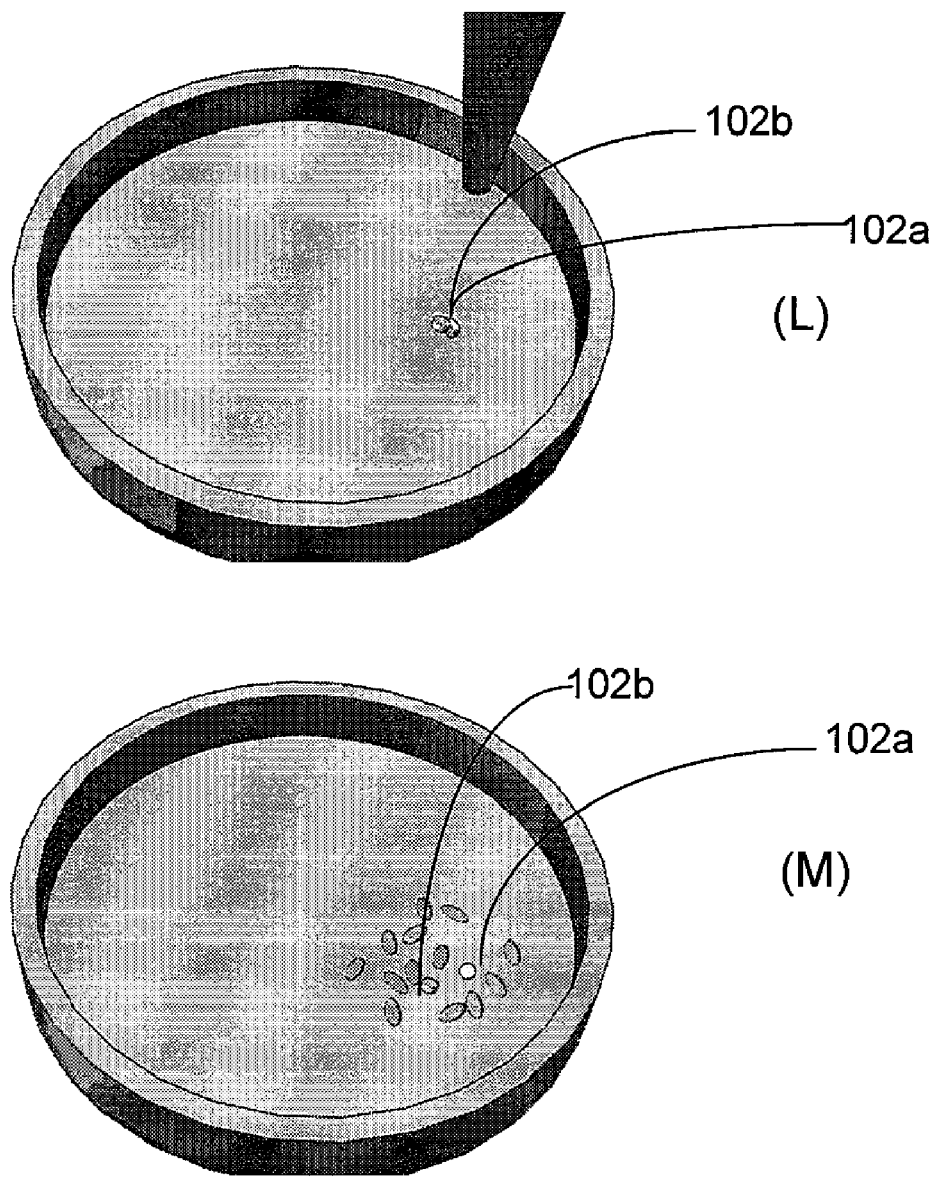
Figure 15:
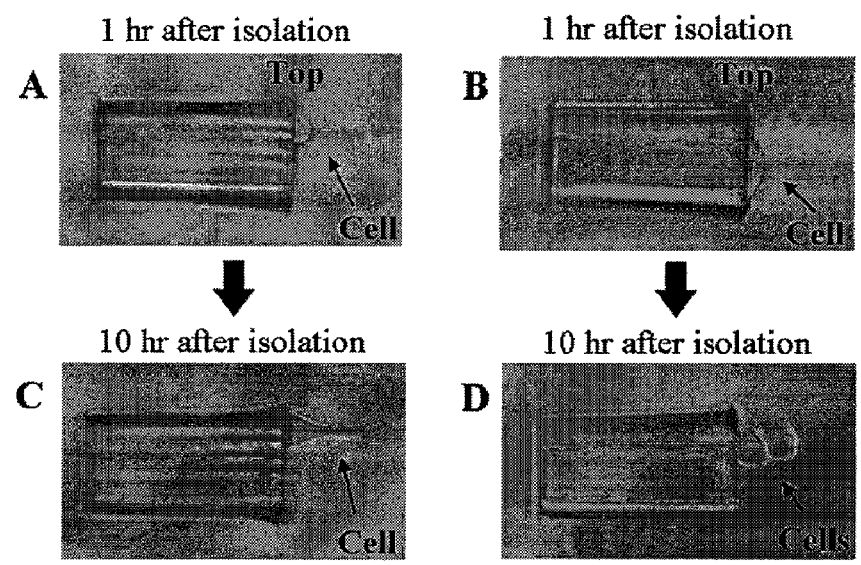
FIGS. 15A through 15D are images showing two examples of individual pallets containing single cells collected from an array and maintained in culture for a 10 hour period demonstrating that single cells remain adherent and viable after isolation and placement in a culture well.
Figure 16:
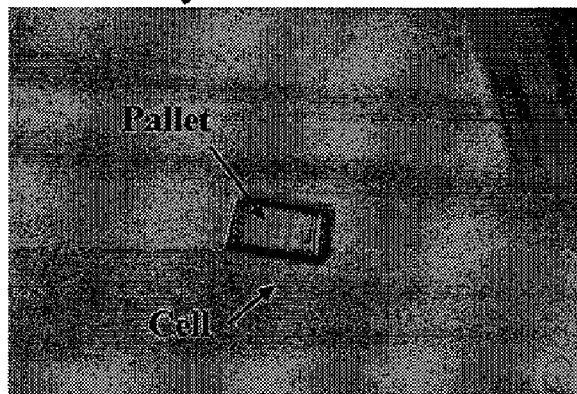
FIG. 16 is an image showing an example of an individual cell obtained from a pallet array which is shown to grow into a clonal colony after collection and isolation in a culture well.
Figure 16:
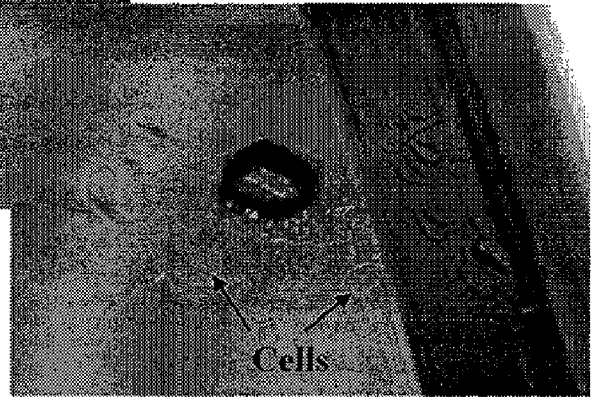
Figure 17:
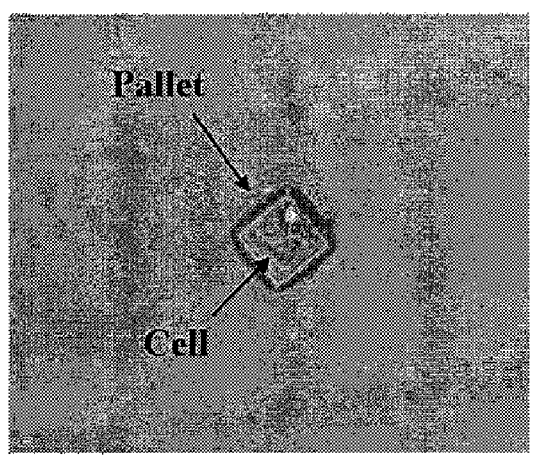
FIGS. 17 is an image showing another example of an individual cell obtained from a pallet array which is shown to grow into a clonal colony after collection and isolation in a culture well.
Figure 17:
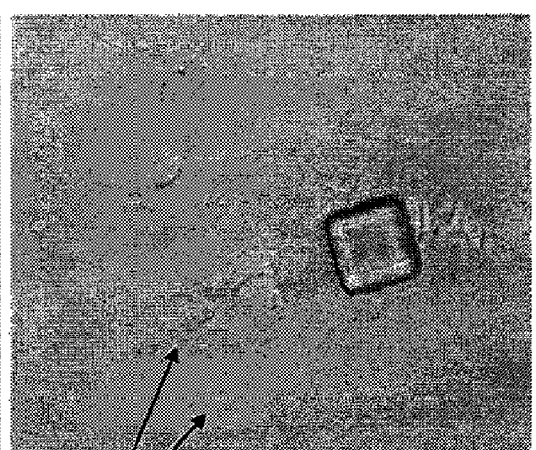

As depicted in FIG. 10 above, cells can be cloned after release from a pallet array. To further document viability after pallet release and to demonstrate that a clonal population can be generated using the pallet selection technique further experiments were performed. To determine whether cells could grow into a colony following pallet release and collection, cells were plated on a pallet array. After 24 hours in culture, individual cells on pallets were released from the array, collected in a multi-well plate, and placed in a standard tissue culture incubator. The cells were imaged within an hour of collection and then at varying times thereafter. At one hour after collection, most cells remained on the pallet tops (see FIG. 15A and B). By 10 hours after collection, most cells had migrated from the pallets onto the adjacent surface and some cells had also undergone cell division (see FIG. 15C and D). Five and seven days following pallet release and collection, many cells were present in those wells plated with cell-containing pallets (see FIGS. 16 and 17). A clonal or genetically identical colony derived from the collected cell on the pallet was present in the wells.

In addition to enabling the use of broader cell selection criteria, the micro-pallet array system also advantageously enable rapid establishment of colonies of stable transfectants. Transfection of cells with DNA to over-express a protein or to express a non-native or a mutant protein is a standard process performed countless times in biology laboratories. Stringent efforts to select small numbers of cells from a large population are required because the incidence of stably transfected cells may be as low as 1 in 10,000. Although modern molecular biology techniques can often achieve high percentages of cells taking up the DNA, it is a fairly rare event for the DNA to be incorporated into the host genome which is required for stable replication and transfer to daughter cells. Cells which are transiently transfected typically lose the foreign DNA and cease to express the protein within a few days in culture. Stably expressing clones of the transfected cells are typically established by antibiotic selection combined with limiting dilution methods. When transfected cells carry a fluorescent marker, flow cytometry may also be employed to sort cells after sufficient time has elapsed to establish adequate numbers of stable clones. Antibiotic selection methods generally require several weeks and significant manpower. In addition, the selection methods themselves can be toxic further decreasing the incidence of stable transfectants.

The rapid loss of expression seen in many transient transfection protocols demonstrates that stable clones can be generated more rapidly than traditional approaches when small clonal colonies of cells are isolated and expanded within days of transfection. When cells are transfected with DNA, clonal colonies still expressing the fusion protein can be isolated in a very few days (e.g., <5-10 days) after transfection. The growth of clonal colonies in these few days can encompass colony sizes within a range of about <50-1000 cells with the number of cell divisions being in a range of about <10-20 cell divisions. These colonies are stably transfected if all progeny of the original cell(s) on the pallet continue to express the gene. The cloned colonies are then rapidly expanded since a colony rather than a single cell is collected. This provides cell biologists with a powerful new tool for rapidly preparing clonal populations with significant reductions in time, manpower and cost.

Figure 18:
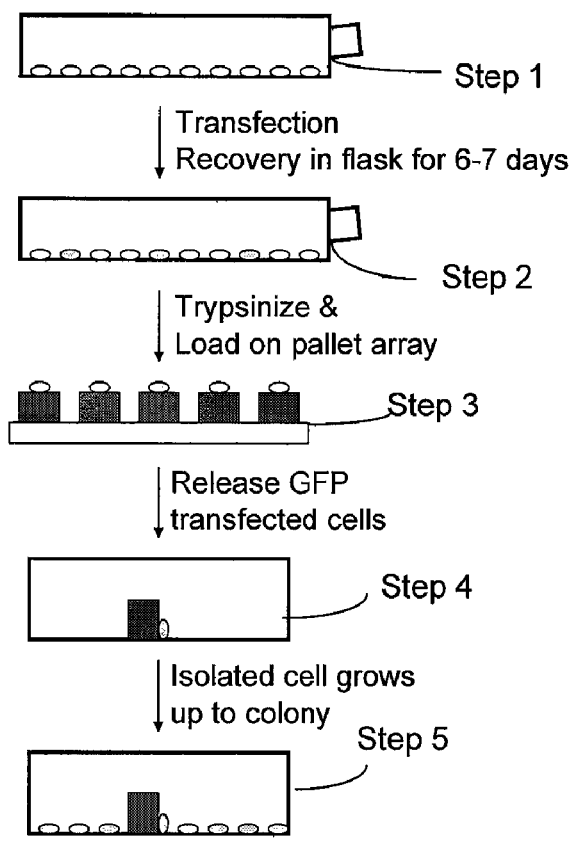
FIG. 18 is a flow chart showing one protocol for establishing a stably transfected cell line using the pallet array.
Figure 19:
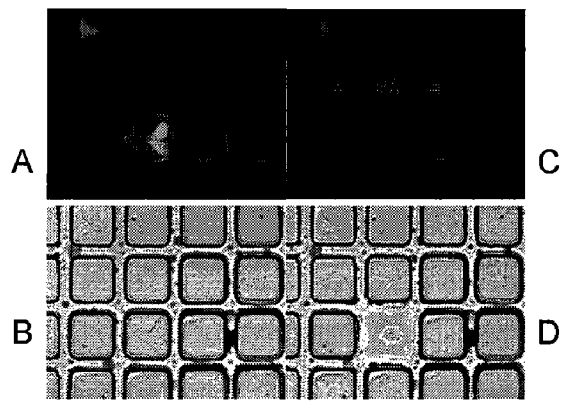
FIGS. 19A, 19B, 19C and 19D are images showing the identification and release (positive selection) of a transfected clone from the cell array generated using the protocol shown in FIG. 18.
Figure 20:
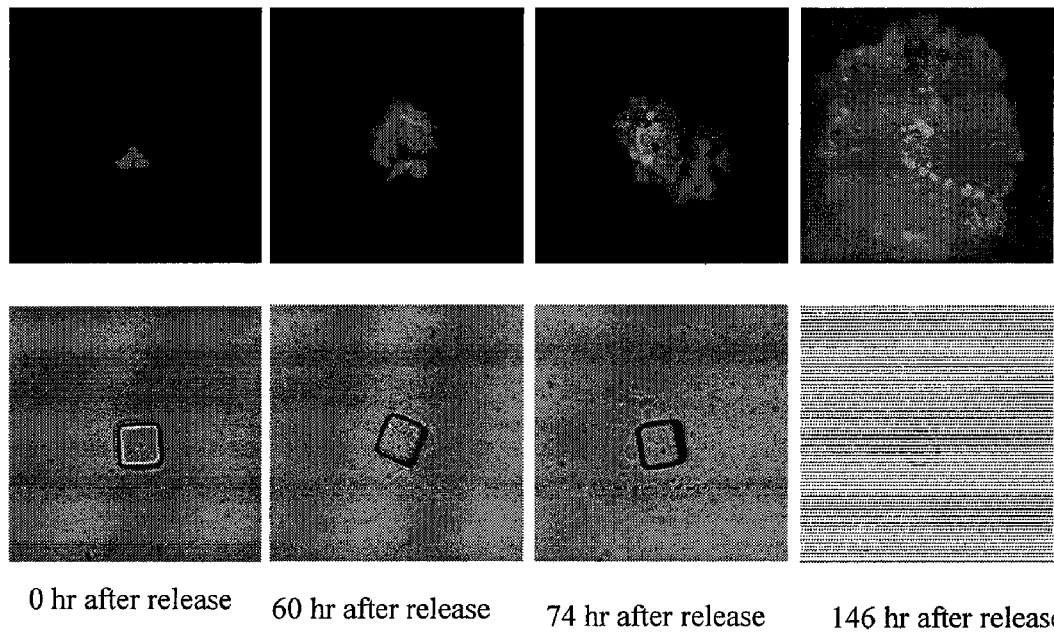
FIG. 20 are images showings the growth of the transfected clone seen in FIG. 19 into a stably transfected colony.

To illustrate the use of the pallet array for the rapid establishment of stable cell lines, a typical experiment is described and illustrated in FIGS. 18 through 20. The first steps include the transfection of the cells (step 1) with the DNA to be expressed, such as that encoding a fluorescent protein, and the recovery of transfectant cells (step 2) within the flask. Any of a variety of transfection vectors may be used including, but not limited to lipid-based carriers, virus, or microorganism. Alternatively electroporation in the presence of the DNA construct can be used. In the depicted protocol, this step is carried out prior to placing the cells on the pallet array and then cells are allowed to recover and proliferate for an appropriate period of time in a culture flask (Step 2). In the next step (step 3) cells are deposited on an array containing pallets each of sufficient surface area to allow growth of a colony of cells of the desired cell number on a single pallet. Cells can be plated from a suspension of the appropriate density and volume so that a majority of pallets contain only a single cell. Alternatively, the array can be screened after cell deposition for pallets with single cells. After plating, pallets containing only one cell are identified and recorded. The array is analyzed over time as the cells grow and multiply. By virtue of the intervening barrier of air between the pallets, cells remain restricted to the pallet on which they originally adhered; therefore, only progeny of the original cell are found on any one pallet. The progeny are scored for the characteristic of interest, such as fluorescence, indicating expression of the target DNA. As indicated in FIGS. 19 and 20, a pallet containing one or more cells bearing the characteristic of interest, here green fluorescence, are released and collected (step 4) and the small clonal colony is allowed to expand (step 5). Stable transfection will result in a colony composed of progeny which all display the characteristic of interest—i.e., green fluorescence. Turning to FIG. 20, the expansion of the clonal colony is shown over time.

Figure 21:
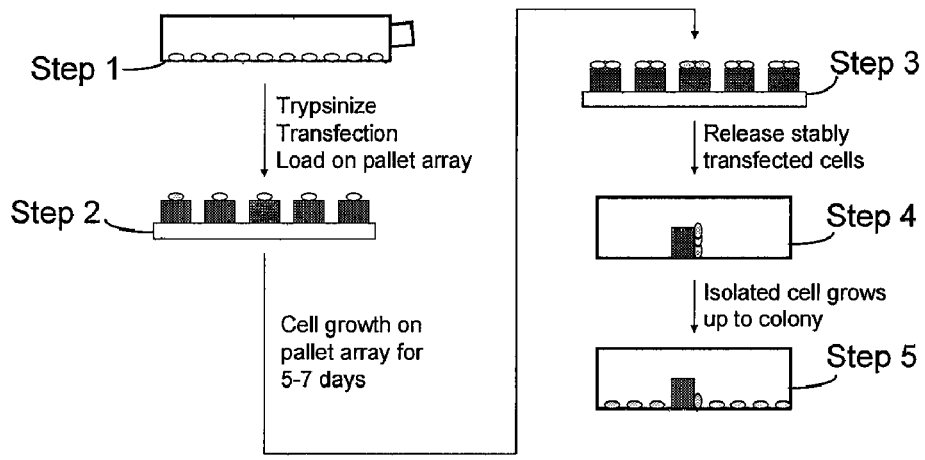
FIG. 21 is a flow chart showing another protocol for more rapidly establishing a stably transfected cell line using the pallet array.
Figure 22:
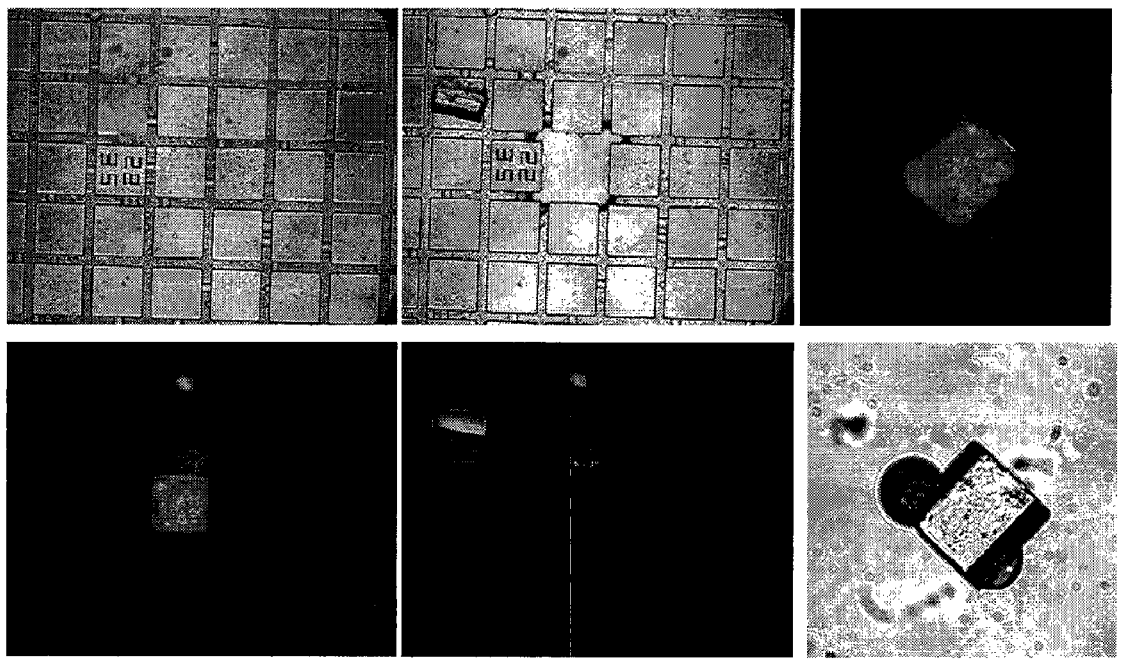
FIG. 22 are images showing the establishment of a stably transfected clonal colony from the cell array generated using the protocol shown in FIG. 21.

Alternatively, as shown in FIG. 21, Stable transfections can be identified and selected even more rapidly by plating cells on the pallet array immediately after the transfection step (Step 1). Cell growth is then carried out on the array for about 5 to 7 days (step 2). As noted above, stable transfection will result in a colony composed of progeny which all display the characteristic of interest—i.e., green fluorescence. In the current example, all progeny in the colony would be fluorescent as a result of expression of the target protein. Cells which are not stably transfected will yield a colony in which there is loss of the characteristic in some or all of the progeny over time. Next, as depicted in FIGS. 21 and 22, the pallets containing stable transfectants—i.e., pallets containing only green fluorescent cells—are released (step 3) and collected (step 4) and the small clonal colony of stable transfectants are allowed to expand (step 5).

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed:

1. A method of collecting a single, living cell comprising the steps of
    arranging a plurality of living cells in an array, wherein each of the plurality of cells is located on a separate pallet within an array of pallets removably coupled to a plate,
    selecting a single living cell from the plurality of living cells, wherein selecting a single living cell includes identifying a cell of interest based on two or more measurements of the cell separated in time, and
    removing the selected living cell from the array by dislodging its pallet from the plate.

2. The method of claim 1 wherein the two or more measurements are made at intervals greater than 1 second.

3. The method of claim 1 wherein the step of selecting includes identifying a cell exhibiting a temporal characteristic of interest.

4. The method of claim 1 wherein the step of selecting includes identifying a cell exhibiting a dynamic characteristic of interest.

5. A method of collecting a single, living cell comprising the steps of
    arranging a plurality of living cells in an array, wherein each of the plurality of cells is located on a separate pallet within an array of pallets removably coupled to a plate, wherein the cell volume is less than 1 nL,
    selecting a single living cell from the plurality of living cells, and
    removing the selected living cell from the array by dislodging its pallet from the plate.

6. The method of claim 5 wherein the cell volume is less than 100 pL.

7. A method of collecting a single, living cell comprising the steps of
    identifying a single living cell in a plurality of living cells based on two or more measurements of the cell separated in time, wherein each of the plurality of cells is located on a separate pallet removably coupled to a plate, and
    separating the selected living cell from the plurality of living cells by dislodging its pallet from the plate.

8. The method of claim 7 wherein the two or more measurements are made at intervals greater than 1 second.

9. The method of claim 7 wherein the step of identifying includes identifying a cell exhibiting a temporal characteristic of interest.

10. The method of claim 7 wherein the step of identifying includes identifying a cell exhibiting a dynamic characteristic of interest.

11. A method of collecting a colony of cells comprising the steps of
    arranging a plurality of colonies of cells in an array, wherein each of the plurality of colonies of cells is located on a separate pallet within an array of pallets removably coupled to a plate, and wherein the cell volume of each cell in the colony is less than 1 nL in volume,
    selecting a colony of cells from the plurality of colonies, and
    removing the selected colony from the array by dislodging its pallet from the plate.

12. The method of claim 11 wherein the colony comprises less than 500 clonal cells.

13. The method of claim 11 wherein the colony comprises less than 100 clonal cells.

14. The method of claim 11 wherein the colony comprises less than 50 clonal cells.

15. The method of claim 11 wherein the cell volume of each cell in the colony is less than 100 pL in volume.

16. The method of claim 11 wherein the cell volume of each cell in the colony is less than 10 pL in volume.

17. A method of collecting a colony of cells comprising the steps of
    arranging a plurality of colonies of cells in an array, wherein each of the plurality of colonies of cells is located on a separate pallet within an array of pallets removably coupled to a plate,
    selecting a colony of cells from the plurality of colonies, wherein the step of selecting includes identifying a colony of interest based on two or more measurements of the colony separated in time, and
    removing the selected colony from the array by dislodging its pallet from the plate.

18. The method of claim 17 wherein the two or more measurements are made at intervals greater than 1 second.

19. The method of claim 17 wherein the step of selecting includes identifying a colony exhibiting a temporal characteristic of interest.

20. The method of claim 17 wherein the step of selecting includes identifying a colony exhibiting a dynamic characteristic of interest.

21. A method comprising the steps of
    transfecting or micromanism-mediated infecting a plurality of cells with DNA of interest, wherein each of the plurality of cells is located on a separate pallet removably coupled to a plate,
    identifying a stable transfectant of a cell from the plurality of cells in less than 5 days after transfection or microrganism-mediated infection of the plurality of cells, and
    collecting the stable transfectant of a cell by dislodging its pallet from the plate.

22. The method of claim 21 wherein the plurality of cells are arranged in an array.

23. The method of claim 21 wherein the cell is adherent to a surface.

24. A method comprising the steps of
transfecting or microrganism-mediated infecting a plurality of cells with DNA of interest, wherein each of the plurality of cells is located on a separate pallet removably coupled to a plate, wherein the cell volume is less than 1 nL
identifying a stable transfectant of a cell from the plurality of cells in less than 10 days after transfection or microrganism-mediated infection of the plurality of cells, and
collecting the stable transfectant of a cell by dislodging its pallet from the plate.

25. The method of claim 24 wherein the cell volume is less than 100 pL.

26. A method comprising the steps of
transfecting or microrganism-mediated infecting a plurality of cells with DNA of interest, wherein each of the plurality of cells is located on a separate pallet removably coupled to a plate,
identifying a stable transfectant of a cell from the plurality of cells in less than 20 cell divisions after transfection or microrganism-mediated infection of the plurality of cells, and
collecting the stable transfectant of a cell by dislodging its pallet from the plate.

27. The method of claim 26 wherein the step of identifying includes identifying the stable transfectant of the cell in less than 10 cell divisions after transfection or microrganism-mediated infection of the plurality of cells.

28. The method of claim 26 wherein the cell volume is less than 1 nL.

29. The method of claim 26 wherein the cell volume is less than 100 pL.

30. The method of claim 26 wherein the plurality of cells are arranged in an array.

31. The method of claim 26 wherein the cell is adherent to a surface.

* * * * *